United States Patent [19]

Rosowsky

[11] Patent Number: 4,490,529

[45] Date of Patent: Dec. 25, 1984

[54] CYSTEIC ACID AND HOMOCYSTEIC ACID ANALOGUES OF METHOTREXATE AND AMINOPTERIN

[75] Inventor: Andre Rosowsky, Needham, Mass.

[73] Assignee: Dana-Farber Cancer Institute, Inc., Boston, Mass.

[21] Appl. No.: 529,214

[22] Filed: Sep. 6, 1983

[51] Int. Cl.³ .......................................... C07D 475/08
[52] U.S. Cl. ................................................. 544/260
[58] Field of Search ........................................ 544/260

[56] References Cited

U.S. PATENT DOCUMENTS 2,742,468  4/1956  Brockman et al. ................ 544/260

OTHER PUBLICATIONS

Seeger et al., J. Am. Chem. Soc., vol. 71, pp. 1753–1758 (1949).

Primary Examiner—Paul M. Coughlan, Jr.

[57] ABSTRACT

Cysteic acid and homocysteic acid analogues of methotrexate and aminopterin having antitumor activity and low toxicity are soluble in water at a physiological pH ranging from 7.2–7.5.

7 Claims, No Drawings

CYSTEIC ACID AND HOMOCYSTEIC ACID ANALOGUES OF METHOTREXATE AND AMINOPTERIN

The invention described herein was made in the course of work under a grant or award from the Department of Health and Human Services and the U.S. government has certain rights in the invention.

The invention relates to certain novel chemical compounds having antitumor activity against L1210 leukemias in mice together with low toxicity and to therapeutic compositions containing these compounds or certain related compounds, together with a pharmaceutically acceptable non-toxic carrier, which are useful for administration to mice and other mammals having certain tumors for extending their life spans.

Methotrexate (MTX; 4-amino-4-deoxy-$N^{10}$-methylpteroylglutamic acid) and Aminopterin (AMT; 4-amino-4-deoxy-pteroylglutamic acid) are folate antagonists and act as antineoplastic agents by interfering with one or more biosynthetic steps involving folate coenzymes of the tumor cell. The structure of MTX differs from AMT in that the former contains a methyl group in the $N^{10}$ position while the latter does not, having hydrogen instead. The structural formula of MTX is as follows:

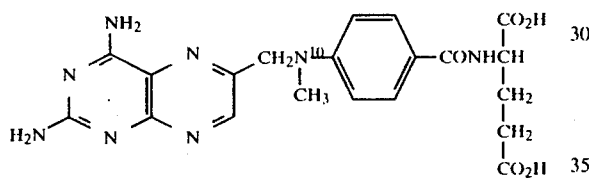

MTX and AMT have been found to be effective clinically against certain malignant tumors: for example, good to excellent tumor response has been seen in patients with acute lymphocytic leukemia, Burkitt's lymphoma, carcinoma of the breast, mycosis fungoides, epidermoid cancer of the head and neck area, and osteogenic sarcoma. In addition, MTX is the drug of choice in the treatment of choriocarcinoma and is also used for certain non-neoplastic conditions such as generalized psoriasis and certain autoimmune diseases such as rheumatoid arthritis and lupus erythematosus.

However, chemotherapy with MTX or AMT is accompanied by a variety of toxicities, partly related to their ability to form polyglutamates, which limit the effectiveness of the compounds and their long-term use.

The novel compounds of the present invention comprise MTX and AMT analogues in which the glutamic acid moiety of MTX or AMT is replaced by cysteic acid or homocysteic acid. These compounds have the following generic structure:

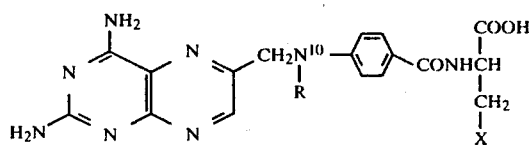

in which R=$CH_3$ or H; X=$SO_3H$ or $CH_2$—$SO_3H$.

The novel compounds of the present invention are prepared by the reaction of 4-amino-4-deoxy-pteroic acid or 4-amino-4-deoxy-$N^{10}$-methylpteroic acid with cysteic or homocysteic acid. Among the compounds of the present invention are:

4-amino-4-deoxy-$N^{10}$-methylpteroyl-D,L-homocysteic acid (mAPA-D,L-HCysA), 4-amino-4-deoxy-$N^{10}$-methylpteroyl-L-cysteic acid (mAPA-L-CysA), 4-amino-4-deoxy-$N^{10}$-methylpteroyl-L-homocysteic acid (mAPA-L-HCysA), 4-amino-4-deoxypteroyl-D,L-homocysteic acid (APA-D,L-HCysA), 4-amino-4-deoxypteroyl-L-cysteic acid (APA-L-CysA), and 4-amino-4-deoxypteroyl-L-homocysteic acid (APA-L-HCysA).

Therapeutic compositions containing the novel compounds of the present invention as the active agents can be prepared by dispersing or dissolving the active agent in any pharmaceutically acceptable non-toxic carrier suitable for the desired mode of administration, which may be parenteral, that is, by injection or infusion which is intravenous, intracavitary, or other conventional mode. Preferably the carrier is an aqueous medium buffered to pH 7.2–7.5, the physiological range. Any suitable conventional buffer can be used such as phosphate, bicarbonate, or citrate. If desired, saline solution can be used, with pH adjustment and buffering. Dosages may vary over a wide range depending upon individual conditions and can readily be determined using the dosages commonly employed for MTX or AMT as exemplars.

The toxicity and therapeutic effectiveness of the compounds of the present invention are shown by in vitro assays and by in vivo evaluations in mice. The cytotoxicity of the compounds against L1210 cells in culture is measured according to the method described by Rosowsky et al. (1982) J. Med. Chem., 25, 171. The results show that cytotoxicity to L1210 cells in culture is comparable to that of MTX or AMT, indicating that the ability of the compounds of the present invention to cross the cell membrane is preserved.

The ability of the compounds of the present invention to act as substrates or inhibitors for the enzymes dihydrofolate reductase and folate polyglutamate synthetase is also measured in in vitro assays.

Dihydrofolate reductase assays are performed as described by Rosowsky et al. (1981) J. Med. Chem. 24, 1450. The results of the dihydrofolate reductase assays show that the compounds of the present invention bind to bacterial (Lactobacillus casei) and mammalian (L1210 mouse leukemia) dihydrofolate reductase with an affinity comparable to MTX and AMT and that changing the distance between the side-chain groups, or replacing the terminal carboxyl group with a sulfonic group, is not detrimental to binding.

Folate polyglutamate synthetase assays are performed as described by Forsch et al. (1983) AACR Proc. 24. The results of the folate polyglutamate synthetase assays show that, unlike MTX and AMT, the compounds of the present invention are poor substrates for the enzyme, and in fact can act as competitive inhibitors when folate is used as the substrate. The inability of the compounds of the present invention to form polyglutamates intracellarly, which presumably accounts for the higher dosage and frequency requirements of these compounds relative to MTX or AMT, is of particular interest and is a therapeutic asset.

In patients with MTX or AMT resistant tumors, where resistance is associated with a lower capacity for polyglutamation than for normal proliferative tissues, dose escalation will be tolerated better with the compounds of the present invention than with MTX or AMT, since the compounds of this invention are not polyglutamated and thus have a faster clearance rate and lower toxicity than MTX or AMT. Thus, the compounds of the present invention whose cytotoxic action does not involve polyglutamation will offer an advantage, since a tumor with a low capacity for polyglutamate formation would be no less sensitive than normal proliferative tissues. Additionally, it should be noted that the compounds of the present invention may find use in longterm low-dose regimens, e.g., in psoriasis or rheumatoid arthritis treatment, where progressive MTX or AMT polyglutamate accumulation in hepatocytes or kidney cells may be responsible for the chronic hepatotoxicity or renal failure typically associated with this type of therapy.

Finally, the compounds of the present invention are the first known compounds to simultaneously inhibit both dihydrofolate reductase and folate polyglutamate synthetase. This dual inhibition of the formation of folate polyglutamates and of the reduction of folates by dihydrofolate reductase classifies the compounds of the present invention as a novel type of "self-potentiating antifolate".

In vivo antitumor activity is determined against L1210 ascitic leukemia in mice according to a standard NCI protocol, Geran et al. (1972) *Cancer Chemother. Rep.*, 3(3), 1. The results of the in vivo antitumor assays against L1210 leukemia in mice show that the compounds of the present invention increase survival to about the same extent as MTX or AMT.

The following examples are intended to illustrate more fully the preparation of the compounds of the present invention without acting as a limitation upon the scope of the invention.

EXAMPLE 1

N-(4-Amino-4-deoxy-$N^{10}$-methylpteroyl)-D,L-homocysteic acid (mAPA-D,L-HCysA)

A suspension of D,L-homocysteic acid (915 mg, 5 mmoles) in dry benzene (25 ml) is treated with triethylamine (2 g, 20 mmoles) and trimethylchlorosilane (2.5 ml, 2.16 g, 20 mmoles). After being stirred at room temperature for 42 hr, the mixture is quickly suction filtered to remove the triethylamine hydrochloride, and the filtrate is evaporated to dryness under reduced pressure to obtain N,O-bis(trimethylsilyl)-D,L-homocysteic acid triethylammonium salt as a pale amber-colored oil or soft semisolid (1.93 g, 90 percent yield). This product is kept protected from atmospheric moisture and used without further purification in the next step.

4-Amino-4-deoxy-$N^{10}$-methylpteroic acid dihydrate (720 mg, 2.0 mmoles) is added in small portions to a stirred solution of diethylphosphorocyanidate (915 mg, 5 mmoles) and triethylamine (500 mg, 5 mmoles) in N,N-dimethylformamide (DMF) (75 ml) previously dried over Linde 4A molecular sieves. The solution is stirred at room temperature overnight, and an extra 25% of diethyl phosphorocyanidate and $Et_3N$ is added. TLC (silica gel, 4:1 chloroform-methanol) indicates the formation of the activated intermediate to be complete. The silylated D,L-homocysteic acid triethylammonium salt (1.8 g, 4 mmoles) is then added, and the reaction mixture is stirred at room temperature for 44 hours. After addition of a few milliliters of water, the solvent is removed with the aid of a rotary evaporator and the residue is dissolved in 3 percent ammonium bicarbonate, with a few drops of concentrated ammonia being added as needed. TLC (cellulose, pH 7.4 phosphate buffer) reveals two spots ($R_f$ 0.4 and 0.8) of unequal size, the faster-moving one being larger. The solution is taken up in a minimum of $H_2O$ with just enough $Nh_4OH$ added to dissolve all the solid, and the solution is applied to a DEAE-cellulose column that has been pre-equilibrated with 3 percent ammonium bicarbonate and then washed to neutrality with $H_2O$. The column is eluted with a large volume of $H_2O$, and then again with 3% $NH_4HCO_3$. The $H_2O$ wash removes salts and some of the impurity with $R_f$ 0.4. Individual 5–10 ml volumes of the $NH_4HCO_3$ eluate are monitored by TLC. Early and late tubes are found to contain a single spot at $R_f$ 0.8, but a number of the tubes in the center of the band are still contaminated with $R_f$ 0.4 material. The by-product eluting with water shows ultraviolet absorption consistent with a 2,4-diaminopteridine structure, but appears to have lost all acidic groups since it is insoluble in concentrated ammonia or 0.1N sodium hydroxide. Its structure is not investigated further. The material eluting from the column in 3 percent ammonium bicarbonate (early and late tubes) is homogeneous by thin-layer chromatography, and on freeze-drying of appropriately pooled eluates a yellow solid is obtained (850 mg, 78 percent yield); m.p. above 300° C., with decomposition. The product, mAPA-D,L-HCysA, is very soluble in water, and in contrast to methotrexate cannot be precipitated from basic solution on adjustment of the pH to 6. Elemental analysis indicates the product to be a hydrated monoammonium salt, presumably of the -sulfonic acid group. Analysis for C, H, N, and S confirms the composition of Example 1.

EXAMPLE 2

N-(4-amino-4-deoxy-$N^{10}$-methylpteroyl)-L-cysteic acid (mAPA-L-CysA)

The same procedure as in the synthesis of Example 1 is followed, except that L-cysteic acid is used instead of D,L-homocysteic acid. The yield of pure mAPA-L-CysA, from pooled early and late fractions of the DEAE-cellulose column is 40% (0.204 gm); IR (KBr)$v$ 3290, 1615sh, 1590 cm$^{-1}$; UV$\lambda_{max}$ (pH 7.4) 258 nm ($\epsilon$ 23,500), 300 (24,100), 372 (7,900); UV$\lambda_{max}$ (0.1N HCl) 239 nm ($\epsilon$ 14,700), 270 (19,400), 341 (5,900). From the contaminated middle fractions was recovered another 0.048 g of mAPA-L-CysA estimated by TLC to be ca. 50% pure. Analysis for C, H, N, and S confirms the composition of Example 2.

EXAMPLE 3

N-(4-amino-4-deoxy-$N^{10}$-methylpteroyl)-L-homocysteic acid (mAPA-L-HCysA)

The same procedure as in the synthesis of Example 1 is followed, except that L-homocysteic acid is used instead of D,L-homocysteic acid and the molar ratio of 4-amino-4-deoxy-$N^{10}$-methylpteroic acid dihydrate to N,O-bis(trimethylsilyl)-L-homocysteic acid is 1.5:2 instead of 1:2. In addition, purification requires two passages through DEAE-cellulose. As in Examples 1 and 2, middle fractions from the DEAE-cellulose column yield material whose TLC indicates that it consists of ca. equal parts of mAPA-L-HCysA and an impurity with $R_f$ 0.4. The yield of pure mAPA-L-HCysA from pooled early and late fractions of the second column was 48%; $R_f$ 0.8 (cellulose, pH 7.4 phosphate); IR (Kbr)$\nu$ 3400, 1640, 1615 cm$^{-1}$; UV$\lambda_{max}$(pH 7.4) 259 nm ($\epsilon$ 24,400), 302 (25,300), 373 (8,200); UV$\lambda_{max}$(0.1N HCl) 242 nm ($\epsilon$ 18,600), 305 (23,000). Analysis for C, H, N, and S confirms the composition of Example 3.

EXAMPLE 4

N-(4-amino-4-deoxypteroyl)-L-cysteic acid (APA-L-CysA)

Aminopterin (2.4 g, 0.005 mol) is suspended in 1M NaOAc (500 ml) containing ZnCl$_2$ (0.1 g), and 2N NaOH is added dropwise with stirring until a clear solution forms. Glacial AcOH is then added dropwise to bring the pH to 7.5, and 5 $\mu$l of carboxypeptidase G$_1$ (4000 units/ml) is added. The mixture is shaken at 37° C. for 1 day, cooled to 5° C., and suction filtered. The solid is washed thoroughly with H$_2$O, and dried in vacuo on a freeze-drying apparatus to obtain 4-amino-4-deoxypteroic acid (APA) (1.43 g, 86%) as an orange-yellow solid. The analytical sample is prepared by passing a small amount of this material through a microcrystalline cellulose column, with 0.1M glycine, pH 10, as the eluent. Appropriate fractions are pooled and acidified with AcOH, and the precipitate is collected, washed with H$_2$O, and dried in vacuo over P$_2$O$_5$; $R_f$ 0.1 (cellulose, pH 7.4 phosphate), dark absorbing spot; UV$\lambda_{max}$ (0.1N HCl) 243 nm ($\epsilon$ 18,500), 297 (23,900), 337 infl (13,700); UV$\lambda_{max}$ (0.1N NaOH) 261 nm ($\epsilon$ 30,400), 371 (9,100). Analysis for C, H, and N confirms the composition of APA.

APA (1.3 g, 0.004 mol) is added, without further purification, to the formylation reagent obtained by combining Ac$_2$O (25 ml) and 98% HCO$_2$H (100 ml) and allowing the heat of reaction to dissipate. When addition of APA to this mixture is complete, the temperature is raised to 100° C. for 1 h. Rotary evaporation and trituration of the residue gives a solid, which is filtered and dried in vacuo on a lyophilizer to obtain 4-amino-4-deoxy-N$^{10}$-formylpteroic acid (N$^{10}$-formyl-APA) as an off-white powder (1.16 g, 82%); $R_f$ 0.4 (cellulose, pH 7.4 phosphate), blue fluorescent spot; UV$\lambda_{max}$ (0.1N HCl) 247 nm ($\epsilon$ 23,100), 337 (9,800); UV$\lambda_{max}$ (pH 7) 258 nm ($\epsilon$ 28,000), 370 (7,200). Analysis for C, H, and N confirms the composition of N$^{10}$-formyl-APA.

A stirred suspension of cysteic acid monohydrate (935 mg, 5.0 mmol) in MeOH (25 ml) cooled in an ice bath is treated dropwise with SOCl$_2$ (5 ml) over 20 min. so that the internal temperature does not exceed 12° C. After being stirred overnight at room temperature the reaction mixture, which is now homogeneous, is evaporated to dryness, and the resulting methyl ester HCl salt is dried in vacuo at 60° C. over P$_2$O$_5$; yield 1.11 g (100%); IR (KBr)$\nu$ 3410, 2940, 1740 (ester C=O) cm$^{-1}$; NMR (D$_2$O) $\delta$3.5 (m, 3H, CH$_2$SO$_3$— and $\alpha$—CH), 3.88 (s, 3H, OCH$_3$). This material is used without further purification in the next step.

To a suspension of N$^{10}$-formyl-APA (187 mg, 0.5 mmol) in dry DMF (20 ml) at room temperature is added Et$_3$N (152 mg, 1.5 mmol) followed by i-BuOCOCl (65 $\mu$l, 68 mg, 0.5 mmol). After 10 min. another 10 $\mu$l of i-BuOCOCl is added to remove residual cloudiness, and 5 min. later the methylester HCL salt of cysteic acid (mCysA) (132 mg, 0.6 mmol) is added in a single portion. Stirring is continued for 15 min., and another 0.75 mmol of Et$_3$N and 0.25 mmol of i-BuOCOCl are added, followed 10 min. later by 0.3 mmol of mCysA. This process was repeated with the same of amounts of reactants, and then carried out one more time with 0.38 mmol of Et$_3$N, 0.13 mmol of i-BuOCOCl, and 0.15 mmol of mCysA. The approximate total of each reactant was thus as follows: N$^{10}$-formyl-APA, 0.5 mmol; Et$_3$N, 3.3 mmol; i-BuOCOCl, 1.1 mmol; mCysA, 1.4 mmol. TLC cellulose, pH 7.4 phosphate) is carried out over the course of the reaction to monitor the disappearance of N$^{10}$-formyl-APA ($R_f$ 0.5, blue fluorescent spot) and concomitant formation of the blocked coupling product 4-amino-4-deoxy-N$^{10l}$ -formylpteroyl-L-cysteic acid ($R_f$ 0.7, blue fluorescent spot). After the final addition of the ester, the reaction mixture is stirred for 10 min. and concentrated to dryness by rotary evaporation, and the residue is taken up in a minimum of H$_2$O. Dropwise addition of 2N NaOH is made until the TLC of the solution ($R_f$ 0.5, dark non-fluorescent spot) shows loss of the N$^{10}$-formyl group. Solid NH$_4$HCO$_3$ is added to bring the pH to 8, and the solution is freeze-dried. The residue is taken up in a minimum of H$_2$O and applied onto a DEAE-cellulose column that has been initially equilibrated with 3% NH$_4$HCO$_3$ and then washed to neutrality with H$_2$O. The column is eluted with H$_2$O to remove salts and with 3% NH$_4$HCO$_3$ to elute the product. Freeze-drying of pooled TLC-homogeneous fractions of the 3% NH$_4$HCO$_3$ eluate gives APA-L-CysA as a bright-yellow powder (189 mg, 72%); IR (KBr)$\nu$ 3030–3230, 1590–1615 cm$^{-1}$; UV$\lambda_{max}$ (pH 7.4) 260 nm ($\epsilon$ 26,900), 282 (25,900), 370 (8,700). Analysis for C, H, N, and S confirms the composition of APA-L-CysA.

EXAMPLE 5

N-(4-Amino-4-deoxypteroyl)-L-homocysteic acid (APA-L-HCysA)

The same procedure as in the synthesis of APA-L-CysA is followed except that L-homocysteic acid is substituted for cysteic acid monohydrate. L-Homocysteic acid (560 mg, 0.3 mmol) is converted to its methyl ester HCl salt (m-L-HCysA) in 80% yield; IR (KBr)$\nu$ 3410, 2940, 1740 (ester C=O) cm$^{-1}$; NMR (D$_2$O) $\delta$2.43 (m, 2H, CH$_2$), 3.0 (m, 3H, CH$_2$SO$_3$— and $\alpha$—CH), 3.87 (s, 3H, OCH$_3$). The mixed anhydride coupling reaction, with TLC monitoring of the disappearance of m-L-HCysA is performed according to the following sequence: (1) N$^{10}$-formyl APA (0.5 mmol), Et$_3$N (1.5 mmol) and i-BuOCOCl (0.5 mmol), 10 min.; (2) i-BuOCOCl (0.08 mmol), 5 min.; (3) m-L-HCysA (0.5 mmol), 10 min.; (4) Et$_3$N (0.75 mmol) and i-BuOCOCl (0.25 mmol), 15 min.; (5) m-L-HCysA (0.25 mmol), 10 min.; (6) Et$_3$N (0.15 mmol) i-BuOCOCl (0.05 mmol), 15 min.; (7) m-L-HCysA (0.05 mmol), 10 min. The yield of APA-L-HCysA after N$^{10}$-formyl cleavage and DEAE-cellulose column chromatography as described above is 223 mg (83%); IR (KBr)$\nu$ 2940–3230, 1625sh, 1585 cm$^{-1}$; UV$\lambda_{max}$(pH 7.4) 260 nm ($\epsilon$ 27,400), 282 (26,100), 370 (8,900); UV$\lambda_{max}$(0.1N HCl) 243 nm ($\epsilon$ 18,300), 290 (20,100). Analysis for C, H, N, and S confirms the composition of APA-L-HCysA.

EXAMPLE 6

N-(4-Amino-4-deoxypteroyl)-D,L-homocysteic acid (APA-D,L-HCysA)

The racemic compound is prepared essentially as in the preceding experiment by substituting D,L-homocysteic acid for L-homocysteic acid. D,L-

Homocysteic acid (366 mg, 2.0 mmol) gives the methyl ester HCl salt (m-D,L-HCysA) in 87% yield as a deliquescent white solid that is stored under vacuum and used without further purification. The mixed anhydride reaction is performed with three cycles of addition of the reactants, in total molar ratios of $N^{10}$-formyl APA (0.5), $Et_3N$ (3.0), i-BuOCOCl (1.1), m-D,L-HCysA (1.1). The final purified yield was 94%. Analysis for C, H, N, and S confirms the composition of APA-D,L-HCysA.

Corresponding D-compounds can be prepared by substituting D-cysteic or D-homocysteic acid for L-cysteic or L-homocysteic acid in the foregoing procedures.

What is claimed is:

1. A compound having the following structure:

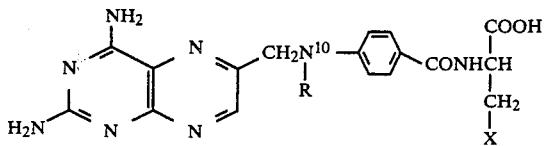

in which R is $CH_3$ or H and X is $SO_3H$ or $CH_2$—$SO_3H$.

2. The compound in claim 1 in which R is $CH_3$ and X is $CH_2$—$SO_3H$ which is 4-amino-4-deoxy-$N^{10}$-methylpteroyl-D,L-homocysteic acid.

3. The compound in claim 1 in which R is $CH_3$ and X is $SO_3H$ which is 4-amino-4-deoxy-$N^{10}$-methylpteroyl-L-cysteic acid.

4. The compound in claim 1 in which R is $CH_3$ and X is $CH_2$—$SO_3H$ which is 4-amino-4-deoxy-$N^{10}$-methylpteroyl-L-homocysteic acid.

5. The compound in claim 1 in which R is H and X is $SO_3H$ which is 4-amino-4-deoxypteroyl-L-cysteic acid.

6. The compound in claim 1 in which R is H and X is $CH_2$—$SO_3H$ which is 4-amino-4-deoxypteroyl-L-homocysteic acid.

7. The compound in claim 1 in which R is H and X is $CH_2$—$SO_3H$ which is 4-amino-4-deoxypteroyl-D,L-homocysteic acid.

* * * * *